(12) United States Patent
Swisher et al.

(10) Patent No.: US 8,162,889 B2
(45) Date of Patent: *Apr. 24, 2012

(54) SAFETY RESET KEY AND NEEDLE ASSEMBLY

(75) Inventors: David Rork Swisher, St. Charles, MO (US); Kimberly A. Moos, Florissant, MO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/892,969

(22) Filed: Sep. 29, 2010

(65) Prior Publication Data

US 2011/0015579 A1 Jan. 20, 2011

Related U.S. Application Data

(63) Continuation of application No. 11/179,090, filed on Jul. 11, 2005, now Pat. No. 7,828,773.

(51) Int. Cl.
*A61M 5/32* (2006.01)

(52) U.S. Cl. ......... 604/162; 604/110; 600/562; 600/567

(58) Field of Classification Search ............... 604/110, 604/192, 198, 162, 164.08; 600/652, 657
See application file for complete search history.

(56) References Cited

U.S. PATENT DOCUMENTS

| | | | |
|---|---|---|---|
| 1,115,561 A | 11/1914 | Northey | |
| 1,436,707 A | 11/1922 | Gaschke | |
| 1,518,531 A | 12/1924 | Lung | |
| 2,219,605 A | 10/1940 | Turkel | |
| 2,854,976 A | 10/1958 | Heydrich | |
| 3,539,034 A | 11/1970 | Tafeen | |
| 3,610,240 A | 10/1971 | Harautuneian | |
| 3,729,998 A | 5/1973 | Mueller et al. | |
| 3,884,230 A | 5/1975 | Wulff | |
| 3,890,971 A | 6/1975 | Leeson et al. | |
| 3,893,058 A | 7/1975 | Keith | |
| 3,893,445 A | 7/1975 | Hofsess | |
| 3,904,033 A | 9/1975 | Haerr | |
| 3,915,003 A | 10/1975 | Adams | |

(Continued)

FOREIGN PATENT DOCUMENTS

DE 3805567 A1 8/1989

(Continued)

OTHER PUBLICATIONS

Office action issued Feb. 3, 2010 in related U.S. Appl. No. 11/179,090, 5 pgs.

(Continued)

*Primary Examiner* — Laura Bouchelle
(74) *Attorney, Agent, or Firm* — Lisa E. Winsor, Esq.

(57) ABSTRACT

A needle assembly includes a mounting structure and a needle mounted on the mounting structure and extending outwardly from the mounting structure. The needle has a longitudinal axis, a sharp end and a central axial passageway. A safety shield is associated with the needle and includes a tubular housing having distal and proximal ends. The distal end of the housing has a funnel-shaped surface. A reset key is configured to engage the distal end of the housing. The reset key includes a support. A shaft extending from the support is adapted for inserting into the distal end the housing. The funnel-shaped surface guides the shaft into the housing to register the reset key with the safety shield.

17 Claims, 11 Drawing Sheets

U.S. PATENT DOCUMENTS

| | | |
|---|---|---|
| 3,976,070 A | 8/1976 | Dumont |
| 4,008,614 A | 2/1977 | Turner et al. |
| 4,010,737 A | 3/1977 | Vilaghy et al. |
| 4,026,287 A | 5/1977 | Haller |
| 4,099,518 A | 7/1978 | Baylis et al. |
| 4,112,762 A | 9/1978 | Turner et al. |
| 4,139,009 A | 2/1979 | Alvarez |
| 4,142,517 A | 3/1979 | Stavropoulos et al. |
| 4,143,853 A | 3/1979 | Abramson |
| 4,160,450 A | 7/1979 | Doherty |
| 4,163,446 A | 8/1979 | Jamshidi |
| 4,177,797 A | 12/1979 | Baylis et al. |
| 4,183,248 A | 1/1980 | West |
| 4,211,214 A | 7/1980 | Chikashige |
| 4,256,119 A | 3/1981 | Gauthier |
| 4,258,713 A | 3/1981 | Wardlaw |
| 4,258,722 A | 3/1981 | Sessions et al. |
| 4,262,676 A | 4/1981 | Jamshidi |
| 4,266,543 A | 5/1981 | Blum |
| 4,266,555 A | 5/1981 | Jamshidi |
| 4,314,565 A | 2/1982 | Lee |
| 4,356,828 A | 11/1982 | Jamshidi |
| 4,392,859 A | 7/1983 | Dent |
| 4,403,617 A | 9/1983 | Tretinyak |
| 4,425,120 A | 1/1984 | Sampson et al. |
| 4,438,884 A | 3/1984 | O'Brien et al. |
| 4,469,109 A | 9/1984 | Mehl |
| 4,482,348 A | 11/1984 | Dent |
| 4,487,209 A | 12/1984 | Mehl |
| 4,513,754 A | 4/1985 | Lee |
| 4,543,966 A | 10/1985 | Islam et al. |
| 4,573,976 A | 3/1986 | Sampson et al. |
| 4,613,329 A | 9/1986 | Bodicky |
| 4,630,616 A | 12/1986 | Tretinyak |
| 4,631,057 A | 12/1986 | Mitchell |
| 4,639,249 A | 1/1987 | Larson |
| 4,643,199 A | 2/1987 | Jennings, Jr. et al. |
| 4,643,200 A | 2/1987 | Jennings, Jr. |
| 4,655,226 A | 4/1987 | Lee |
| 4,664,654 A | 5/1987 | Strauss |
| 4,676,783 A | 6/1987 | Jagger et al. |
| 4,681,567 A | 7/1987 | Masters et al. |
| 4,693,708 A | 9/1987 | Wanderer et al. |
| 4,695,274 A | 9/1987 | Fox |
| 4,723,943 A | 2/1988 | Spencer |
| 4,725,267 A | 2/1988 | Vaillancourt |
| 4,728,320 A | 3/1988 | Chen |
| 4,735,619 A | 4/1988 | Sperry et al. |
| 4,737,144 A | 4/1988 | Choksi |
| 4,738,663 A | 4/1988 | Bogan |
| 4,743,233 A | 5/1988 | Schneider |
| 4,747,831 A | 5/1988 | Kulli |
| 4,747,836 A | 5/1988 | Luther |
| 4,747,837 A | 5/1988 | Hauck |
| 4,752,290 A | 6/1988 | Schramm |
| 4,762,516 A | 8/1988 | Luther et al. |
| 4,770,655 A | 9/1988 | Haber et al. |
| 4,772,272 A | 9/1988 | McFarland |
| 4,775,363 A | 10/1988 | Sandsdalen |
| 4,781,684 A | 11/1988 | Trenner |
| 4,781,692 A | 11/1988 | Jagger et al. |
| 4,785,826 A | 11/1988 | Ward |
| 4,790,329 A | 12/1988 | Simon |
| 4,790,827 A | 12/1988 | Haber et al. |
| 4,790,828 A | 12/1988 | Dombrowski et al. |
| 4,793,363 A | 12/1988 | Ausherman et al. |
| 4,795,432 A | 1/1989 | Karczmer |
| 4,804,372 A | 2/1989 | Laico et al. |
| 4,810,248 A | 3/1989 | Masters et al. |
| 4,813,426 A | 3/1989 | Haber et al. |
| 4,816,022 A | 3/1989 | Poncy |
| 4,819,659 A | 4/1989 | Sitar |
| 4,820,275 A | 4/1989 | Haber et al. |
| 4,826,488 A | 5/1989 | Nelson et al. |
| 4,826,490 A | 5/1989 | Byrne et al. |
| 4,826,491 A | 5/1989 | Schramm |
| 4,834,718 A | 5/1989 | McDonald |
| 4,838,280 A | 6/1989 | Haaga |
| 4,838,282 A | 6/1989 | Strasser et al. |
| 4,842,586 A | 6/1989 | Hogan |
| 4,846,809 A | 7/1989 | Sims |
| 4,900,307 A | 2/1990 | Kulli |
| 4,904,242 A | 2/1990 | Kulli |
| 4,906,235 A | 3/1990 | Roberts |
| 4,909,793 A | 3/1990 | Vining et al. |
| 4,911,694 A | 3/1990 | Dolan |
| 4,911,706 A | 3/1990 | Levitt |
| 4,915,702 A | 4/1990 | Haber |
| 4,922,602 A | 5/1990 | Mehl |
| 4,927,414 A | 5/1990 | Kulli |
| 4,929,241 A | 5/1990 | Kulli |
| 4,931,044 A | 6/1990 | Beiter |
| 4,935,013 A | 6/1990 | Haber et al. |
| 4,943,283 A | 7/1990 | Hogan |
| 4,944,725 A | 7/1990 | McDonald |
| 4,950,250 A | 8/1990 | Haber et al. |
| 4,952,207 A | 8/1990 | Lemieux |
| 4,955,866 A | 9/1990 | Corey |
| 4,958,625 A | 9/1990 | Bates et al. |
| 4,960,412 A | 10/1990 | Fink |
| 4,964,854 A | 10/1990 | Luther |
| 4,966,587 A | 10/1990 | Baumgart |
| 4,969,554 A | 11/1990 | Sawaya |
| 4,978,344 A | 12/1990 | Dombrowski et al. |
| 4,986,279 A | 1/1991 | O'Neill |
| 5,005,585 A | 4/1991 | Mazza |
| 5,012,818 A | 5/1991 | Joishy |
| 5,013,304 A | 5/1991 | Russell et al. |
| 5,031,634 A | 7/1991 | Simon |
| 5,036,860 A | 8/1991 | Leigh et al. |
| 5,047,044 A | 9/1991 | Smith et al. |
| 5,049,136 A | 9/1991 | Johnson |
| 5,051,109 A | 9/1991 | Simon |
| 5,053,017 A | 10/1991 | Chamuel |
| 5,057,085 A | 10/1991 | Kopans |
| 5,059,180 A | 10/1991 | McLees |
| 5,085,648 A | 2/1992 | Purdy et al. |
| 5,092,851 A | 3/1992 | Ragner |
| 5,102,394 A | 4/1992 | Lasaitis et al. |
| 5,108,374 A | 4/1992 | Lemieux |
| 5,109,849 A | 5/1992 | Goodman et al. |
| 5,126,090 A | 6/1992 | Egolf et al. |
| 5,127,916 A | 7/1992 | Spencer et al. |
| 5,133,727 A | 7/1992 | Bales et al. |
| 5,135,504 A | 8/1992 | McLees |
| 5,154,703 A | 10/1992 | Bonaldo |
| 5,171,229 A | 12/1992 | McNeil et al. |
| 5,176,256 A | 1/1993 | Sawaya |
| 5,183,468 A | 2/1993 | McLees |
| 5,195,533 A | 3/1993 | Chin et al. |
| 5,195,985 A | 3/1993 | Hall |
| 5,213,115 A | 5/1993 | Zytkovicz et al. |
| 5,215,525 A | 6/1993 | Sturman |
| 5,215,528 A | 6/1993 | Purdy et al. |
| 5,215,533 A | 6/1993 | Robb |
| 5,217,438 A | 6/1993 | Davis et al. |
| 5,228,451 A | 7/1993 | Bales et al. |
| 5,256,149 A | 10/1993 | Banik et al. |
| 5,257,632 A | 11/1993 | Turkel et al. |
| 5,279,563 A | 1/1994 | Brucker et al. |
| 5,279,591 A | 1/1994 | Simon |
| 5,282,477 A | 2/1994 | Bauer |
| 5,295,977 A | 3/1994 | Cohen et al. |
| 5,304,136 A | 4/1994 | Erskine et al. |
| 5,312,359 A | 5/1994 | Wallace |
| 5,314,406 A | 5/1994 | Arias et al. |
| 5,316,013 A | 5/1994 | Striebel, II et al. |
| 5,320,635 A | 6/1994 | Smith |
| 5,322,517 A | 6/1994 | Sircom et al. |
| 5,324,288 A | 6/1994 | Billings et al. |
| 5,328,482 A | 7/1994 | Sircom et al. |
| 5,331,972 A | 7/1994 | Wadhwani et al. |
| 5,334,158 A | 8/1994 | McLees |
| 5,338,311 A | 8/1994 | Mahurkar |
| 5,338,314 A | 8/1994 | Ryan |
| 5,341,816 A | 8/1994 | Allen |
| 5,344,408 A | 9/1994 | Partika |

| | | | | | |
|---|---|---|---|---|---|
| 5,348,022 A | 9/1994 | Leigh et al. | 5,630,837 A | 5/1997 | Crowley |
| 5,348,544 A | 9/1994 | Sweeney et al. | 5,634,473 A | 6/1997 | Goldenberg et al. |
| 5,356,421 A | 10/1994 | Castro | 5,643,307 A | 7/1997 | Turkel et al. |
| 5,357,974 A | 10/1994 | Baldridge | 5,656,031 A | 8/1997 | Thorne et al. |
| 5,368,045 A | 11/1994 | Clement et al. | 5,662,610 A | 9/1997 | Sircom |
| 5,368,046 A | 11/1994 | Scarfone et al. | 5,669,883 A | 9/1997 | Scarfone et al. |
| 5,370,623 A | 12/1994 | Kreamer | 5,672,161 A | 9/1997 | Allen et al. |
| 5,385,151 A | 1/1995 | Scarfone et al. | 5,679,907 A | 10/1997 | Ruck |
| 5,385,570 A | 1/1995 | Chin et al. | 5,685,852 A | 11/1997 | Turkel et al. |
| 5,389,104 A | 2/1995 | Hahnen et al. | 5,687,907 A | 11/1997 | Holden |
| 5,389,106 A | 2/1995 | Tower | 5,690,619 A | 11/1997 | Erskine |
| 5,394,885 A | 3/1995 | Francese | 5,693,022 A | 12/1997 | Haynes |
| 5,395,375 A | 3/1995 | Turkel et al. | 5,695,467 A | 12/1997 | Miyata et al. |
| 5,396,900 A | 3/1995 | Slater et al. | 5,695,521 A | 12/1997 | Anderhub |
| 5,399,167 A | 3/1995 | Deniega | 5,697,904 A | 12/1997 | Raines et al. |
| 5,403,283 A | 4/1995 | Luther | 5,697,907 A | 12/1997 | Gaba |
| 5,405,323 A | 4/1995 | Rogers et al. | 5,700,249 A | 12/1997 | Jenkins |
| 5,405,388 A | 4/1995 | Fox | 5,700,250 A | 12/1997 | Erskine |
| 5,409,461 A | 4/1995 | Steinman | 5,702,080 A | 12/1997 | Whittier et al. |
| 5,411,486 A | 5/1995 | Zadini et al. | 5,702,369 A | 12/1997 | Mercereau |
| 5,415,182 A | 5/1995 | Chin et al. | 5,706,824 A | 1/1998 | Whittier |
| 5,417,659 A | 5/1995 | Gaba | 5,707,392 A | 1/1998 | Kortenbach |
| 5,417,709 A | 5/1995 | Slater | 5,713,368 A | 2/1998 | Leigh |
| 5,419,766 A | 5/1995 | Chang et al. | 5,713,888 A | 2/1998 | Neuenfeldt et al. |
| 5,421,522 A | 6/1995 | Bowen | 5,715,832 A | 2/1998 | Koblish et al. |
| 5,423,766 A | 6/1995 | Di Cesare | 5,718,688 A | 2/1998 | Wozencroft |
| 5,425,718 A | 6/1995 | Tay et al. | 5,722,422 A | 3/1998 | Palmer et al. |
| 5,425,884 A | 6/1995 | Botz | 5,730,150 A | 3/1998 | Peppel et al. |
| 5,429,138 A | 7/1995 | Jamshidi | 5,730,724 A | 3/1998 | Plishka et al. |
| 5,429,616 A | 7/1995 | Schaffer | 5,735,827 A | 4/1998 | Adwers et al. |
| 5,454,378 A | 10/1995 | Palmer et al. | 5,738,665 A | 4/1998 | Caizza et al. |
| 5,456,267 A | 10/1995 | Stark | 5,746,753 A | 5/1998 | Sullivan et al. |
| 5,458,658 A | 10/1995 | Sircom | 5,752,923 A | 5/1998 | Terwilliger |
| 5,462,062 A | 10/1995 | Rubinstein et al. | D395,609 S | 6/1998 | Knieriem et al. |
| 5,466,223 A | 11/1995 | Bressler et al. | 5,758,655 A | 6/1998 | Como Rodriguez et al. |
| 5,471,992 A | 12/1995 | Banik et al. | 5,776,157 A | 7/1998 | Thorne et al. |
| 5,473,629 A | 12/1995 | Muramoto | 5,795,336 A | 8/1998 | Romano et al. |
| 5,476,099 A | 12/1995 | Robinson et al. | 5,807,275 A | 9/1998 | Jamshidi |
| 5,476,102 A | 12/1995 | Como et al. | 5,807,277 A | 9/1998 | Swaim |
| 5,478,313 A | 12/1995 | White | 5,810,744 A | 9/1998 | Chu et al. |
| 5,480,385 A | 1/1996 | Thorne et al. | 5,817,069 A | 10/1998 | Arnett |
| 5,482,054 A | 1/1996 | Slater et al. | 5,823,970 A | 10/1998 | Terwilliger |
| 5,487,734 A | 1/1996 | Thorne et al. | 5,823,997 A | 10/1998 | Thorne |
| 5,492,532 A | 2/1996 | Ryan et al. | 5,824,002 A | 10/1998 | Gentelia et al. |
| 5,501,675 A | 3/1996 | Erskine | D400,808 S | 11/1998 | Schwan |
| 5,507,297 A | 4/1996 | Slater et al. | 5,836,917 A | 11/1998 | Thorne et al. |
| 5,507,298 A | 4/1996 | Schramm et al. | 5,836,921 A | 11/1998 | Mahurkar |
| 5,514,152 A | 5/1996 | Smith | 5,840,044 A | 11/1998 | Dassa et al. |
| 5,522,398 A | 6/1996 | Goldenberg et al. | 5,843,001 A | 12/1998 | Goldenberg |
| 5,526,821 A | 6/1996 | Jamshidi | 5,848,692 A | 12/1998 | Thorne et al. |
| 5,533,516 A | 7/1996 | Sahatjian | 5,853,393 A | 12/1998 | Bogert |
| 5,533,974 A | 7/1996 | Gaba | 5,860,955 A | 1/1999 | Wright et al. |
| 5,538,009 A | 7/1996 | Byrne et al. | 5,865,806 A | 2/1999 | Howell |
| 5,542,927 A | 8/1996 | Thorne et al. | 5,871,453 A | 2/1999 | Banik et al. |
| 5,549,565 A | 8/1996 | Ryan et al. | 5,873,886 A | 2/1999 | Larsen et al. |
| 5,549,708 A | 8/1996 | Thorne et al. | 5,879,332 A | 3/1999 | Schwemberger et al. |
| 5,553,624 A | 9/1996 | Francese et al. | 5,879,337 A | 3/1999 | Kuracina et al. |
| 5,558,651 A | 9/1996 | Crawford et al. | 5,879,338 A | 3/1999 | Mahurkar |
| 5,562,629 A | 10/1996 | Haughton et al. | 5,882,337 A | 3/1999 | Bogert et al. |
| 5,562,633 A | 10/1996 | Wozencroft | 5,893,845 A | 4/1999 | Newby et al. |
| 5,562,683 A | 10/1996 | Chan | 5,895,361 A | 4/1999 | Turturro |
| 5,569,299 A | 10/1996 | Dill et al. | 5,897,507 A | 4/1999 | Kortenbach et al. |
| 5,570,783 A | 11/1996 | Thorne et al. | 5,906,594 A | 5/1999 | Scarfone et al. |
| 5,573,008 A | 11/1996 | Robinson et al. | 5,910,130 A | 6/1999 | Caizza et al. |
| 5,573,510 A | 11/1996 | Isaacson | 5,910,132 A | 6/1999 | Schultz |
| 5,578,015 A | 11/1996 | Robb | 5,913,859 A | 6/1999 | Shapira |
| 5,584,809 A | 12/1996 | Gaba | 5,916,175 A | 6/1999 | Bauer |
| 5,584,810 A | 12/1996 | Brimhall | 5,928,163 A | 7/1999 | Roberts et al. |
| 5,584,818 A | 12/1996 | Morrison | 5,935,109 A | 8/1999 | Donnan |
| 5,586,990 A | 12/1996 | Hahnen et al. | 5,951,489 A | 9/1999 | Bauer |
| 5,591,202 A | 1/1997 | Slater et al. | 5,951,525 A | 9/1999 | Thorne et al. |
| 5,595,186 A | 1/1997 | Rubinstein et al. | 5,951,582 A | 9/1999 | Thorne et al. |
| 5,599,310 A | 2/1997 | Bogert | 5,954,696 A | 9/1999 | Ryan |
| 5,601,585 A | 2/1997 | Banik et al. | 5,954,698 A | 9/1999 | Pike |
| 5,601,599 A | 2/1997 | Nunez | 5,957,887 A | 9/1999 | Osterlind et al. |
| 5,615,690 A | 4/1997 | Giurtino et al. | 5,957,892 A | 9/1999 | Thorne |
| 5,623,969 A | 4/1997 | Raines | 5,961,526 A | 10/1999 | Chu et al. |
| 5,624,459 A | 4/1997 | Kortenbach et al. | 5,964,717 A | 10/1999 | Gottlieb et al. |
| 5,630,506 A | 5/1997 | Thorne et al. | 5,967,490 A | 10/1999 | Pike |

| | | | | | | |
|---|---|---|---|---|---|---|
| 5,976,115 | A | 11/1999 | Parris et al. | 6,501,384 B2 | 12/2002 | Chapman et al. |
| 5,979,840 | A | 11/1999 | Hollister et al. | 6,517,516 B1 | 2/2003 | Caizza |
| 5,989,196 | A | 11/1999 | Chu et al. | 6,519,569 B1 | 2/2003 | White et al. |
| 5,989,229 | A | 11/1999 | Chiappetta | 6,520,938 B1 | 2/2003 | Funderburk et al. |
| 5,989,241 | A | 11/1999 | Plishka et al. | 6,537,255 B1 | 3/2003 | Raines |
| 5,993,426 | A | 11/1999 | Hollister | 6,537,259 B1 | 3/2003 | Niermann |
| 6,000,846 | A | 12/1999 | Gregory et al. | 6,551,328 B2 | 4/2003 | Kortenbach |
| 6,004,294 | A | 12/1999 | Brimhall et al. | 6,554,778 B1 | 4/2003 | Fleming, III |
| 6,015,391 | A | 1/2000 | Rishton et al. | 6,569,125 B2 | 5/2003 | Jepson et al. |
| 6,022,324 | A | 2/2000 | Skinner | 6,575,919 B1 | 6/2003 | Reiley et al. |
| 6,024,727 | A | 2/2000 | Thorne et al. | 6,582,402 B1 | 6/2003 | Erskine |
| 6,033,369 | A | 3/2000 | Goldenberg | 6,582,446 B1 | 6/2003 | Marchosky |
| 6,036,675 | A | 3/2000 | Thorne et al. | 6,585,704 B2 | 7/2003 | Luther et al. |
| 6,047,729 | A | 4/2000 | Hollister et al. | 6,592,556 B1 | 7/2003 | Thorne |
| 6,050,954 | A | 4/2000 | Mittermeier | 6,595,954 B1 | 7/2003 | Luther et al. |
| 6,050,976 | A | 4/2000 | Thorne et al. | 6,595,955 B2 | 7/2003 | Ferguson et al. |
| 6,063,037 | A | 5/2000 | Mittermeier et al. | 6,613,018 B2 | 9/2003 | Bagga et al. |
| 6,063,040 | A | 5/2000 | Owen et al. | 6,616,604 B1 | 9/2003 | Bass et al. |
| 6,071,284 | A | 6/2000 | Fox | 6,616,630 B1 | 9/2003 | Woehr et al. |
| 6,080,115 | A | 6/2000 | Rubinstein | 6,623,458 B2 | 9/2003 | Woehr et al. |
| 6,083,176 | A | 7/2000 | Terwilliger | 6,626,850 B1 | 9/2003 | Chau et al. |
| 6,083,202 | A | 7/2000 | Smith | D480,977 S | 10/2003 | Wawro et al. |
| 6,086,563 | A | 7/2000 | Moulton et al. | 6,629,959 B2 | 10/2003 | Kuracina et al. |
| 6,090,078 | A | 7/2000 | Erskine | 6,635,003 B2 | 10/2003 | Marchant |
| 6,090,108 | A | 7/2000 | McBrayer et al. | 6,638,252 B2 | 10/2003 | Moulton et al. |
| 6,095,967 | A | 8/2000 | Black et al. | 6,638,254 B2 | 10/2003 | Nakagami |
| 6,096,005 | A | 8/2000 | Botich et al. | 6,652,486 B2 | 11/2003 | Bialecki et al. |
| 6,106,484 | A | 8/2000 | Terwilliger | 6,652,490 B2 | 11/2003 | Howell |
| 6,110,128 | A | 8/2000 | Andelin et al. | 6,663,592 B2 | 12/2003 | Rhad et al. |
| 6,110,129 | A | 8/2000 | Terwilliger | 6,673,047 B2 | 1/2004 | Crawford et al. |
| RE36,885 | E | 9/2000 | Blecher et al. | 6,673,060 B1 | 1/2004 | Fleming, III |
| 6,117,108 | A | 9/2000 | Woehr et al. | 6,682,510 B2 | 1/2004 | Niermann |
| 6,117,112 | A | 9/2000 | Mahurkar | 6,689,102 B2 | 2/2004 | Greene |
| 6,117,115 | A | 9/2000 | Hill et al. | 6,692,471 B2 | 2/2004 | Boudreaux |
| 6,132,401 | A | 10/2000 | Van Der Meyden et al. | 6,698,921 B2 | 3/2004 | Siefert |
| 6,135,110 | A | 10/2000 | Roy | 6,699,221 B2 | 3/2004 | Vaillancourt |
| 6,142,957 | A | 11/2000 | Diamond et al. | 6,702,786 B2 | 3/2004 | Olovson |
| 6,149,629 | A | 11/2000 | Wilson et al. | 6,709,419 B2 | 3/2004 | Woehr |
| 6,171,284 | B1 | 1/2001 | Kao et al. | 6,719,732 B2 | 4/2004 | Courteix |
| 6,193,671 | B1 | 2/2001 | Turturro et al. | 6,723,075 B2 | 4/2004 | Davey et al. |
| 6,197,007 | B1 | 3/2001 | Thorne et al. | 6,727,805 B2 | 4/2004 | Hollister et al. |
| 6,203,527 | B1 | 3/2001 | Zadini et al. | 6,730,043 B2 | 5/2004 | Krueger et al. |
| 6,210,373 | B1 | 4/2001 | Allmon | 6,731,216 B2 | 5/2004 | Ho et al. |
| 6,217,556 | B1 | 4/2001 | Ellingson et al. | 6,749,576 B2 | 6/2004 | Bauer |
| 6,221,029 | B1 | 4/2001 | Mathis et al. | 6,749,588 B1 | 6/2004 | Howell et al. |
| 6,221,047 | B1 | 4/2001 | Greene et al. | 6,749,595 B1 | 6/2004 | Murphy |
| 6,224,569 | B1 | 5/2001 | Brimhall | 6,755,793 B2 | 6/2004 | Lamoureux et al. |
| 6,224,576 | B1 | 5/2001 | Thorne et al. | 6,761,704 B2 | 7/2004 | Crawford |
| 6,234,773 | B1 | 5/2001 | Hill et al. | 6,761,706 B2 | 7/2004 | Vaillancourt |
| 6,254,575 | B1 | 7/2001 | Thorne, Jr. et al. | 6,764,567 B2 | 7/2004 | Sperko et al. |
| 6,280,399 | B1 | 8/2001 | Rossin et al. | 6,767,336 B1 | 7/2004 | Kaplan |
| 6,280,401 | B1 | 8/2001 | Mahurkar | 6,770,050 B2 | 8/2004 | Epstein |
| 6,280,419 | B1 | 8/2001 | Vojtasek | 6,796,962 B2 | 9/2004 | Ferguson et al. |
| 6,280,420 | B1 | 8/2001 | Ferguson et al. | 6,798,348 B1 | 9/2004 | Wilker et al. |
| D448,314 | S | 9/2001 | Chen | 6,811,308 B2 | 11/2004 | Chapman et al. |
| 6,283,925 | B1 | 9/2001 | Terwilliger | 6,821,267 B2 | 11/2004 | Veillon, Jr. et al. |
| 6,287,278 | B1 | 9/2001 | Woehr et al. | 6,827,488 B2 | 12/2004 | Knieriem et al. |
| 6,293,700 | B1 | 9/2001 | Lund et al. | 6,832,992 B2 | 12/2004 | Wilkinson |
| 6,302,852 | B1 | 10/2001 | Fleming, III et al. | 6,839,651 B2 | 1/2005 | Lantz et al. |
| 6,309,376 | B1 | 10/2001 | Alesi | 6,846,314 B2 | 1/2005 | Shapira |
| 6,312,394 | B1 | 11/2001 | Fleming, III | 6,849,051 B2 | 2/2005 | Sramek et al. |
| 6,315,737 | B1 | 11/2001 | Skinner | 6,855,128 B2 | 2/2005 | Swenson |
| 6,321,782 | B1 | 11/2001 | Hollister | 6,855,130 B2 | 2/2005 | Saulenas et al. |
| 6,322,537 | B1 | 11/2001 | Chang | 6,875,183 B2 | 4/2005 | Cervi |
| 6,334,857 | B1 | 1/2002 | Hollister et al. | 6,890,308 B2 | 5/2005 | Islam |
| 6,340,351 | B1 | 1/2002 | Goldenberg | 6,902,546 B2 | 6/2005 | Ferguson |
| 6,358,265 | B1 | 3/2002 | Thorne, Jr. et al. | 6,916,292 B2 | 7/2005 | Morawski et al. |
| 6,361,525 | B2 | 3/2002 | Capes et al. | 6,916,314 B2 | 7/2005 | Schneider et al. |
| 6,379,333 | B1 | 4/2002 | Brimhall et al. | 6,923,813 B2 | 8/2005 | Phillips et al. |
| 6,379,338 | B1 | 4/2002 | Garvin | 6,936,036 B2 | 8/2005 | Wilkinson et al. |
| 6,383,144 | B1 | 5/2002 | Mooney et al. | D512,506 S | 12/2005 | Layne et al. |
| 6,406,459 | B1 | 6/2002 | Allmon | D512,924 S | 12/2005 | Ikeda |
| 6,409,701 | B1 | 6/2002 | Cohn et al. | 6,981,948 B2 | 1/2006 | Pellegrino et al. |
| 6,416,484 | B1 | 7/2002 | Miller et al. | 6,983,062 B2 | 1/2006 | Smith |
| 6,443,910 | B1 | 9/2002 | Krueger et al. | 6,984,213 B2 | 1/2006 | Horner et al. |
| 6,443,927 | B1 | 9/2002 | Cook | 6,984,216 B2 | 1/2006 | Sendijarevic et al. |
| 6,478,751 | B1 | 11/2002 | Krueger et al. | 6,989,003 B2 | 1/2006 | Wing et al. |
| 6,485,473 | B1 | 11/2002 | Lynn | 7,001,363 B2 | 2/2006 | Ferguson et al. |
| 6,488,663 | B1 | 12/2002 | Steg | 7,004,927 B2 | 2/2006 | Ferguson et al. |

| | | | |
|---|---|---|---|
| 7,018,343 B2 | 3/2006 | Plishka | |
| 7,021,842 B2 | 4/2006 | Yamada et al. | |
| 7,033,324 B2 | 4/2006 | Giusti et al. | |
| 7,036,984 B2 | 5/2006 | Penney et al. | |
| 7,063,703 B2 | 6/2006 | Reo | |
| 7,108,679 B2 | 9/2006 | Alchas | |
| 7,112,191 B2 | 9/2006 | Daga | |
| 7,118,552 B2 | 10/2006 | Shaw et al. | |
| 7,147,607 B2 | 12/2006 | Wang | |
| 7,179,244 B2 | 2/2007 | Smith et al. | |
| 7,204,812 B2 | 4/2007 | Wang | |
| 7,207,973 B2 | 4/2007 | Barrelle | |
| 7,226,434 B2 | 6/2007 | Carlyon et al. | |
| 7,238,169 B2 | 7/2007 | Takagi et al. | |
| 7,247,148 B2 | 7/2007 | Murashita | |
| 7,300,420 B2 | 11/2007 | Doyle | |
| 7,341,573 B2 | 3/2008 | Ferguson et al. | |
| 7,377,908 B2 | 5/2008 | Buetikofer et al. | |
| 7,413,562 B2 | 8/2008 | Ferguson et al. | |
| 7,458,954 B2 | 12/2008 | Ferguson et al. | |
| 7,488,306 B2 | 2/2009 | Nguyen | |
| 7,500,965 B2 | 3/2009 | Menzi et al. | |
| 7,513,888 B2 | 4/2009 | Sircom et al. | |
| 7,517,348 B2 | 4/2009 | Vetter et al. | |
| 7,530,965 B2 | 5/2009 | Villa et al. | |
| 7,601,139 B2 | 10/2009 | Woehr et al. | |
| 7,641,620 B2 | 1/2010 | Wingler | |
| 7,662,108 B2 | 2/2010 | Dunker et al. | |
| 7,798,993 B2 | 9/2010 | Lim et al. | |
| 2003/0114797 A1 | 6/2003 | Vaillancourt et al. | |
| 2003/0176810 A1 | 9/2003 | Maahs et al. | |
| 2003/0220617 A1 | 11/2003 | Dickerson | |
| 2004/0071182 A1 | 4/2004 | Quinn et al. | |
| 2004/0077973 A1 | 4/2004 | Groenke et al. | |
| 2004/0153005 A1 | 8/2004 | Krueger | |
| 2004/0236288 A1 | 11/2004 | Howell et al. | |
| 2005/0027263 A1 | 2/2005 | Woehr et al. | |
| 2005/0054987 A1 | 3/2005 | Perez et al. | |
| 2005/0070850 A1 | 3/2005 | Albrecht | |
| 2005/0070851 A1 | 3/2005 | Thompson et al. | |
| 2005/0075609 A1 | 4/2005 | Latona | |
| 2005/0113716 A1 | 5/2005 | Mueller, Jr. et al. | |
| 2005/0131345 A1 | 6/2005 | Miller | |
| 2005/0165404 A1 | 7/2005 | Miller | |
| 2005/0192536 A1 | 9/2005 | Takagi et al. | |
| 2005/0267383 A1 | 12/2005 | Groenke et al. | |
| 2005/0273057 A1 | 12/2005 | Popov | |
| 2005/0277845 A1 | 12/2005 | Cooke et al. | |
| 2006/0064101 A1 | 3/2006 | Arramon | |
| 2006/0116603 A1 | 6/2006 | Shibazaki et al. | |
| 2006/0189936 A1 | 8/2006 | Carlyon et al. | |
| 2006/0200195 A1 | 9/2006 | Yang | |
| 2006/0276772 A1 | 12/2006 | Moos et al. | |

FOREIGN PATENT DOCUMENTS

| | | | |
|---|---|---|---|
| EP | 1358846 A1 | | 11/2003 |
| JP | 6241914 A | | 9/1994 |
| WO | 9622800 A1 | | 8/1996 |
| WO | 9742989 A1 | | 11/1997 |
| WO | 2005053774 A1 | | 6/2004 |
| WO | 2004060138 | | 7/2004 |
| WO | 2004091687 A2 | | 10/2004 |
| WO | 2005009246 | | 2/2005 |
| WO | WO 2005053774 A1 | * | 6/2005 |
| WO | 2005060679 A2 | | 7/2005 |

OTHER PUBLICATIONS

Response filed May 3, 2010 to Office Action dated Feb. 3, 2010 from related U.S. Appl. No. 11/179,090, 8 pgs.

Office action issued Feb. 4, 2010 in related U.S. Appl. No. 11/179,438, 7 pgs.

Response filed May 4, 2010 to Office Action dated Feb. 4, 2010 from related U.S. Appl. No. 11/179,438, 10 pgs.

Office action issued Jul. 27, 2010 in related U.S. Appl. No. 11/179,438, 9 pgs.

Office action issued Jan. 11, 2010 in related U.S. Appl. No. 11/179,696, 8 pgs.

Response filed May 10, 2010 to Office Action dated Jan. 11, 2010 from related U.S. Appl. No. 11/179,696, 8 pgs.

Office action issued Jul. 6, 2010 in related U.S. Appl. No. 11/741,529, 13 pgs.

Response filed Oct. 6, 2010 to Office Action dated Jul. 6, 2010 from related U.S. Appl. No. 11/741,529, 11 pgs.

* cited by examiner

SAFETY RESET KEY AND NEEDLE ASSEMBLY

CROSS-REFERENCE TO RELATED APPLICATIONS

This application is a continuation of U.S. Ser. No. 11/179,090, filed Jul. 11, 2005, the entirety of which is incorporated herein by reference.

BACKGROUND OF THE INVENTION

This invention relates generally to needle assemblies and more particularly to needle assemblies that have shields to cover sharp ends of needles.

Needle assemblies of the present invention have particular, although not exclusive application in the field of medicine and have needles with sharpened ends for use in piercing the skin to withdraw materials as needed. The needle is supported by some other structure that is used to manipulate the needle. The most common example is a syringe. However, some needle assemblies require the application of substantial force in use. One example of such a needle assembly is a bone marrow needle assembly that is used to penetrate cortical bone to reach the intramedullary canal for withdrawing liquid or a biopsy sample of bore marrow, or for infusing the canal with a selected material. Typically, the needle includes a cannula and a stylet that is received in the cannula and has a hard, sharp tip that can penetrate cortical bone. The tip projects out from the distal end of the cannula. The stylet can be withdrawn from the cannula after the needle penetrates the bone so that the hollow interior of the cannula can be used as a conduit for liquid or a receptacle to collect bone marrow.

In order to penetrate cortical bone, a substantial amount of force must be applied to the needle. For this reason, bone needle assemblies conventionally mount the needle in a handle that is sized and shaped so that the technician may comfortably grip the handle and apply the force necessary to penetrate the bone. The handle may comprise two handle members that can be selectively put together and separated for inserting the stylet into the cannula and removing the stylet from the cannula. A proximal handle member mounts the stylet and a distal handle member mounts the cannula. "Proximal" and "distal" refer to the relative location of the handle members to the technician when the needle assembly is in use. The proximal handle member is in contact with the palm of the technician's hand in use, and the distal handle member is on the opposite side of the proximal handle member from the palm.

Some needle assemblies, including bone needle assemblies, have associated safety mechanisms that shield the sharp tips of the needle components when they are not needed and after they have become contaminated with potentially hazardous biological material. The safety mechanism includes a shield and usually a mechanism for locking the shield in place over the sharpened tip. As a matter of convenience, and to enhance the probability that the safety feature will be used by a medical technician, the safety feature may be secured to the needle assembly. However, the safety feature must be retained out of the way when the needle assembly is being used, for example, to collect a liquid or solid sample from the intramedullary canal. The safety feature then must be released from its stowed position and moved to an operative position in which its shield covers the sharpened tip of the needle.

In cases where a sample (e.g., a bone marrow sample) is collected by the needle assembly, the sample has to be removed from the needle assembly. An obturator is a device including a long thin shaft, and in some cases includes a blunt tip, that can fit inside the cannula for pushing the sample of bone marrow out of the cannula. This can be done with the safety shield in position covering the sharp end of the cannula to protect the technician. In some cases it will be determined that the sample is not satisfactory and it will be necessary to obtain a second sample. It is not necessary to use a new needle assembly, because the needle assembly would be reused on the same patient. However, the shield is held in place over the tip of the needle assembly making it unusable for a collecting a second sample. Accordingly, there is a need for a needle assembly that can be easily reset for second use, but which will not result in inadvertent release of the safety shield.

SUMMARY OF THE INVENTION

In one aspect of the present invention, a needle assembly generally comprises a mounting structure and a needle mounted on the mounting structure and extending outwardly therefrom. The needle has a longitudinal axis, a sharp end and a central axial passageway. A safety shield is associated with the needle and includes a tubular housing having distal and proximal ends. The distal end of the housing has a funnel-shaped surface. A reset key is configured to engage the distal end of the housing. The reset key includes a support. A shaft extends from the support for inserting into the distal end of the housing. The funnel-shaped surface guides the shaft into the housing to register the reset key with the safety shield.

In another aspect of the present invention, a safety shield for shielding a sharp end of a needle generally comprises a tubular housing adapted for movement relative to the needle. The housing includes distal and proximal ends. The distal end of the housing has a funnel-shaped surface and is adapted to receive a shaft extending from a support of a reset key. The funnel-shaped surface guides the shaft into the housing to register the reset key with the safety shield.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
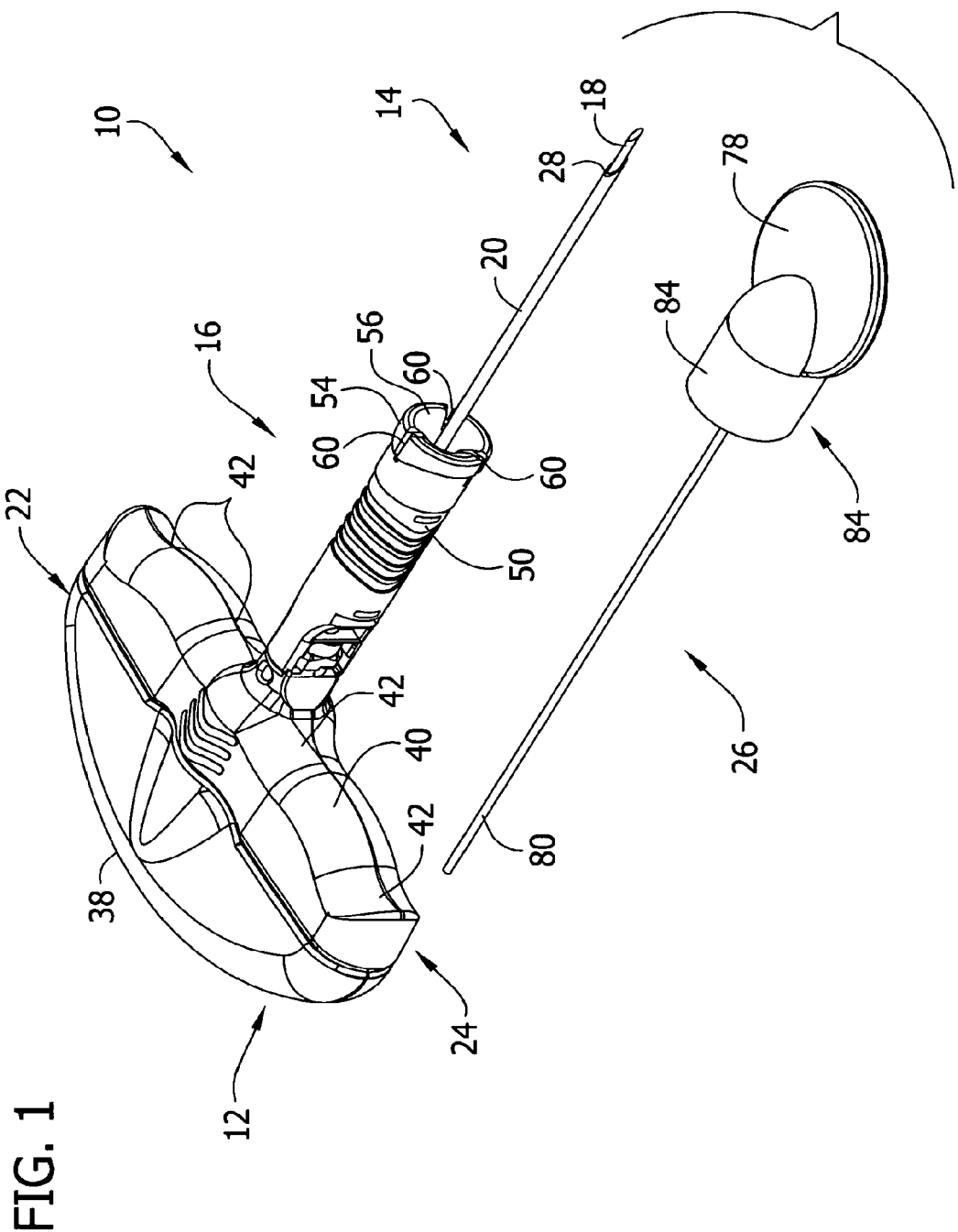
FIG. 1 is a perspective of a bone needle assembly including an obturator.

Referring now to the drawings and in particular to FIG. 1, a medical instrument constructed according to the principles of the present invention is shown in the form of a bone needle assembly, generally indicated at 10. The bone needle assembly includes a handle 12 (broadly, "mounting structure"), a needle 14 and a cannula safety shield 16, all reference numbers indicating their subjects generally. The needle 14 includes a stylet 18 and a cannula 20 that can receive the stylet. The handle 12 includes a first or proximal handle member (indicated generally at 22) mounting the stylet 18, and a second or distal handle member (indicated generally at 24) mounting the cannula 20. It will be understood that a needle could include only a single component part, or more than two parts within the scope of the present invention. Similarly, a handle could be a single part or more than two parts. The mounting structure for a needle can be other than a handle without departing from the present invention. The needle assembly 10 further includes an obturator 26, which is described more fully below, that may be used to remove a sample captured in the cannula 20.

The cannula 20 has a central axial passage extending the length of the cannula and opening at both ends of the cannula. A distal tip 28 of the cannula 20 is beveled and sharpened, and a proximal end portion of the cannula 20 is received in the distal handle member 24. The stylet 18 is solid and includes a sharp distal tip, and a proximal end portion of the stylet is received in the proximal handle member 22. The stylet 18 can be inserted through the central axial passage opening in the proximal end portion of the cannula 20 and received entirely through the axial passage of the cannula so that its sharp distal tip projects axially outward from the distal tip 28 of the cannula (as shown in FIG. 1). The stylet 18 provides the tool for penetrating the cortical bone, and can be removed from the cannula 20 once the intramedullary canal is accessed by the needle 14.

The handle 12 formed by the proximal and distal handle members 22, 24 has an ergonomic shape that can be comfortably received in a medical technician's hand, and allows the technician to easily control the needle assembly 10 as he or she applies the substantial forces needed to penetrate the bone. More specifically, the top or proximal surface 38 of the proximal handle member 22 is rounded in conformance with the shape of the palm of the hand. The bottom or distal surface 40 of the distal handle member 24 is also rounded, but is undulating in shape thereby forming finger wells 42 for receiving the technician's fingers. The form of the handle can be other than described herein without departing from the scope of the present invention. Moreover, needle mounting structure can be other than a handle within the scope of the present invention. The proximal and distal handle members 22, 24 can be connected together in a suitable manner when the stylet 18 is received in the cannula 20, so that the handle 12 acts essentially as a single piece when used to drive the needle 14 through a patient's skin and into the bone. The proximal and distal handle members 22, 24 can be disconnected and moved apart for removing the stylet 18 from the cannula 20.

The cannula safety shield 16 may be moved to cover the distal tip 28 of the cannula 20 after the needle assembly 10 has been used. The safety shield 16 includes a generally tubular housing 50 and an internal locking mechanism (generally indicated at 52 in FIG. 2) capable of releasably locking the tubular housing in position covering the distal tip 28 of the cannula 20. The tubular housing 50 has a proximal end closer to the handle 12 and a distal end farther away from the handle. A distal end piece of the tubular housing 50 (generally indicated at 54) includes a funnel-shaped distal end surface 56 of the tubular housing 50 and a central aperture 58 generally aligned with the central axial passageway of the cannula 20. Although illustrated as a separately formed part attached to the tubular housing 50, the distal end piece 54 and tubular housing may be formed as a single piece of material. The shape of the distal end surface 56 may be other than described (e.g., lying in a plane perpendicular to the longitudinal axis of the cannula 20) within the scope of the present invention. Three slots 60 located on the periphery of the tubular housing distal end piece 54 each extend radially inwardly from the periphery of the end piece at its distal end and also extend axially along the end piece toward the proximal end of the tubular housing 50. The number of slots and their precise configuration may be other than described without departing from the scope of the present invention. The function of the slots 60 will be described hereinafter. The tubular housing 50 and handle 12 may include structure to secure the tubular housing in a retracted position adjacent the handle when not needed. An example of such structure is shown in co-assigned U.S. application Ser. No. 11/146,173, filed Jun. 6, 2005, the disclosure of which is incorporated herein by reference.

The locking mechanism 52 inside the safety shield 16 comprises a canting member including a base 62 having a hole and a pair of arms 64 (only one is shown) extending generally axially from the base. The arms 64 are connected together by a U-shaped member 66 at their ends and each has an upwardly (as oriented in the figures) bent tab 68 (only one is shown) projecting axially outward from the end. Before the locking mechanism 52 is activated to lock the tubular housing 50 in position, the ends of the arms 64 ride on the exterior surface of the cannula 20. This holds the canting member so that the base 62 is generally orthogonal so the longitudinal axis of the cannula 20 and the base can move along the cannula (with the safety shield 16), with the cannula sliding substantially unimpeded through the hole in the base. Once the ends of the arms 64 pass the distal tip 28 of the cannula 20, the locking mechanism 52 is constructed so that the ends of the arms move in a generally radial direction toward an opposite side of the longitudinal axis of the cannula 20. This causes the base 62 of the canting member to cant relative to the axis of the cannula 20 so that the hole in the base is no longer orthogonal to the axis of the cannula. As a result, the base 62 at the edge of the hole grippingly engages the cannula 20 to lock the safety shield 16 in place. The locking mechanism 52 further includes angled surfaces 69A, 69B fixed to the tubular housing 50 that can engage the canting member base 62 to keep the canting member in its canted, locking position upon movement of the tubular housing 50 in either direction relative to the cannula 20. It will be understood that a locking mechanism could take on other forms than shown and described without departing from the scope of the present invention.

The safety shield 16 further includes an annular reset plunger 70 located inside the tubular housing 50 near its distal end. The reset plunger 70 is movable axially relative to the housing 50 toward the proximal end and includes a frusto-conically shaped front surface 72 that is engageable with the tabs 68 of the locking mechanism to release the locking mechanism, as will be more fully described hereinafter. A spring 74 engages the reset plunger 70 and biases it toward the distal end of the tubular housing 50. Thus, unless the reset plunger 70 is forcibly moved, it normally does not interfere with the operation of the locking mechanism 52.

The needle assembly 10 is driven into the bone by grasping the handle 12 and pushing the stylet 18 through the skin, underlying tissue and cortical bone. Once this penetration has been achieved, the stylet 18 is no longer required. The proximal handle member 22 is disconnected from the distal handle member 24 and moved axially away from the distal handle member so that the stylet 18 slides out of the central axial passageway of the cannula 20 while the cannula remains in the bone. In order to collect a sample of bone marrow, the distal handle member 24 is advanced further into the bone. The sharp tip 28 of the cannula 20 cuts into the bone marrow and a sample is received in the central axial passageway of the cannula. The cannula 20 can then be withdrawn from the patient by pulling on the distal handle member 24. The sample remains lodged in the central axial passageway of the cannula 20 near the sharp tip 28. It will be understood that a needle assembly may be used to collect a sample other than of bone marrow within the scope of the present invention. Moreover, it is not necessary that a cannula be used to collect any sample. For instance, the cannula could also be used to withdraw or infuse fluid.

Figure 6:
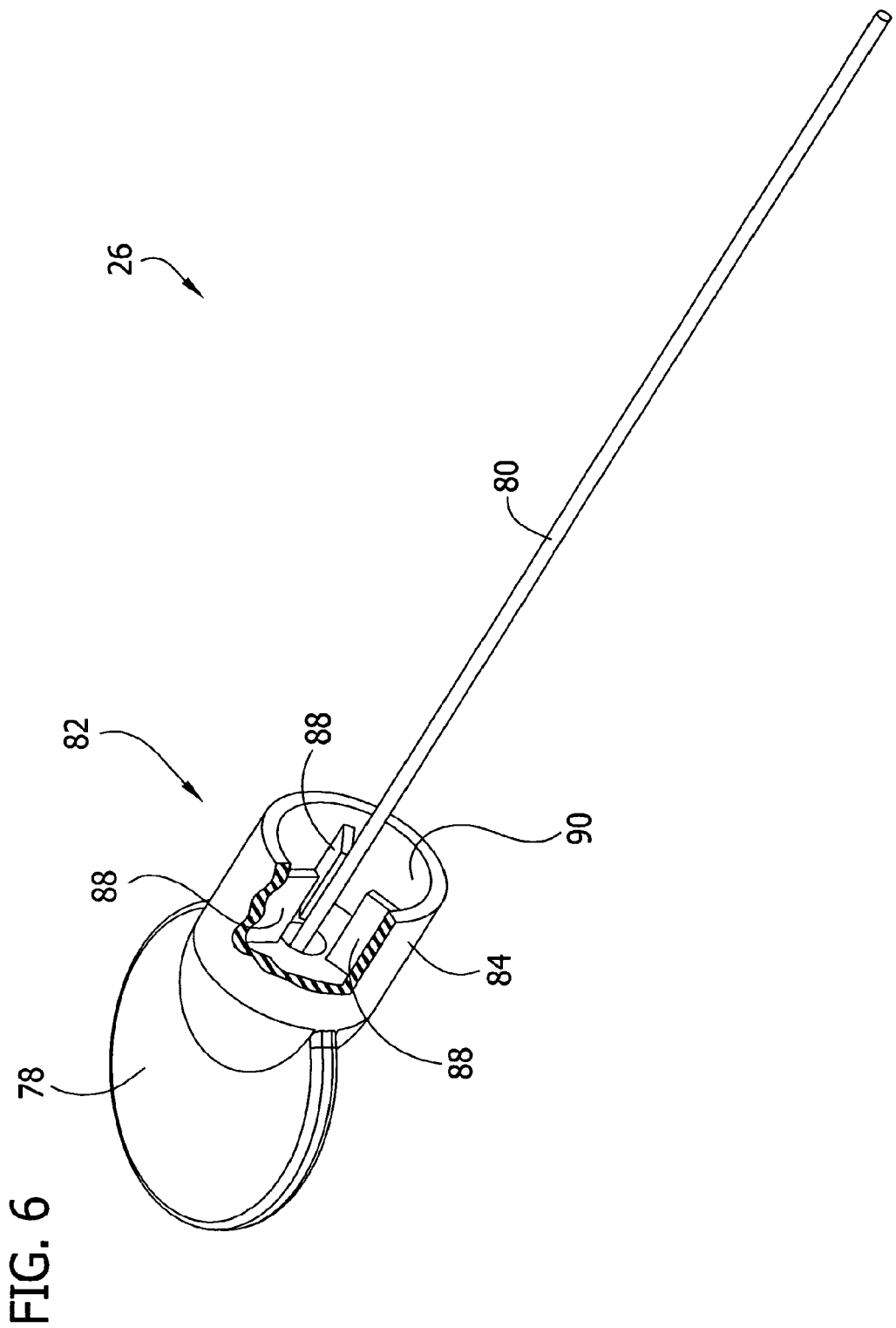
FIG. 6 is a fragmentary perspective of the obturator with parts broken away to show internal construction.
Figure 7:
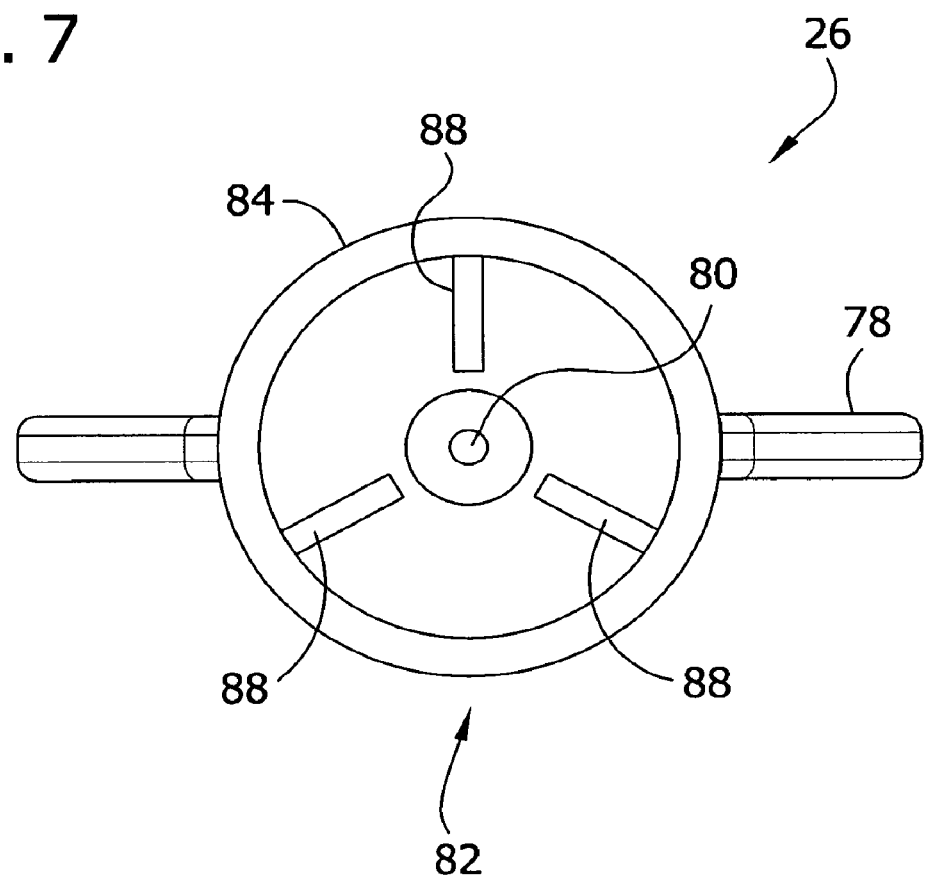
FIG. 7 is an end view of the obturator.
Figure 8:
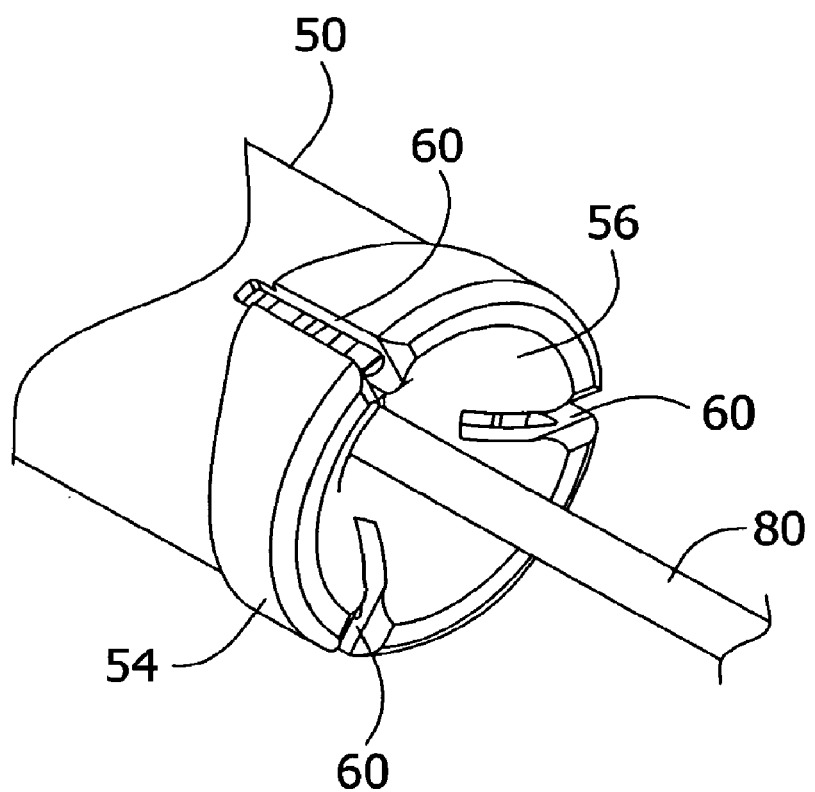
FIG. 8 is a fragmentary perspective of the obturator entering the safety shield.

The obturator 26 is used to remove a lodged sample of bone marrow that has been collected in the central axial passageway of cannula 20. The obturator 26 includes a grip 78 and a long, thin shaft 80 extending from the grip that is sized to be received in the central axial passageway of the cannula 20 in generally close fitting relation therein. The grip 78 is sized and shaped to be grasped by a user (e.g., between the thumb and pointer finger) for manipulating the obturator 26, as will be described. As shown best in FIGS. 6 and 7, a reset key, generally indicated 82, extends from the grip 78 in the same direction as the shaft 80, and as illustrated is formed as one piece of material with the grip. In the illustrated embodiment, the reset key 82 comprises a tubular shroud 84 (broadly, "a support") defining a central open space 86 sized and shaped to receive a portion of the tubular housing 50 therein. Although shown as a solid tubular piece of material with an open end, the shroud 84 need not be solid around its circumference within the scope of the present invention. Three elongate ribs 88 formed on an inner wall 90 of the tubular shroud 84 extend generally parallel to the axis of the shroud and are arranged for reception in the slots 60 of the tubular housing 50 as will be described. It will be appreciated that a reset key (not shown) may not be part of an obturator (i.e., the reset key would not include a shaft like shaft 80) without departing from the scope of the present invention.

Figure 2:
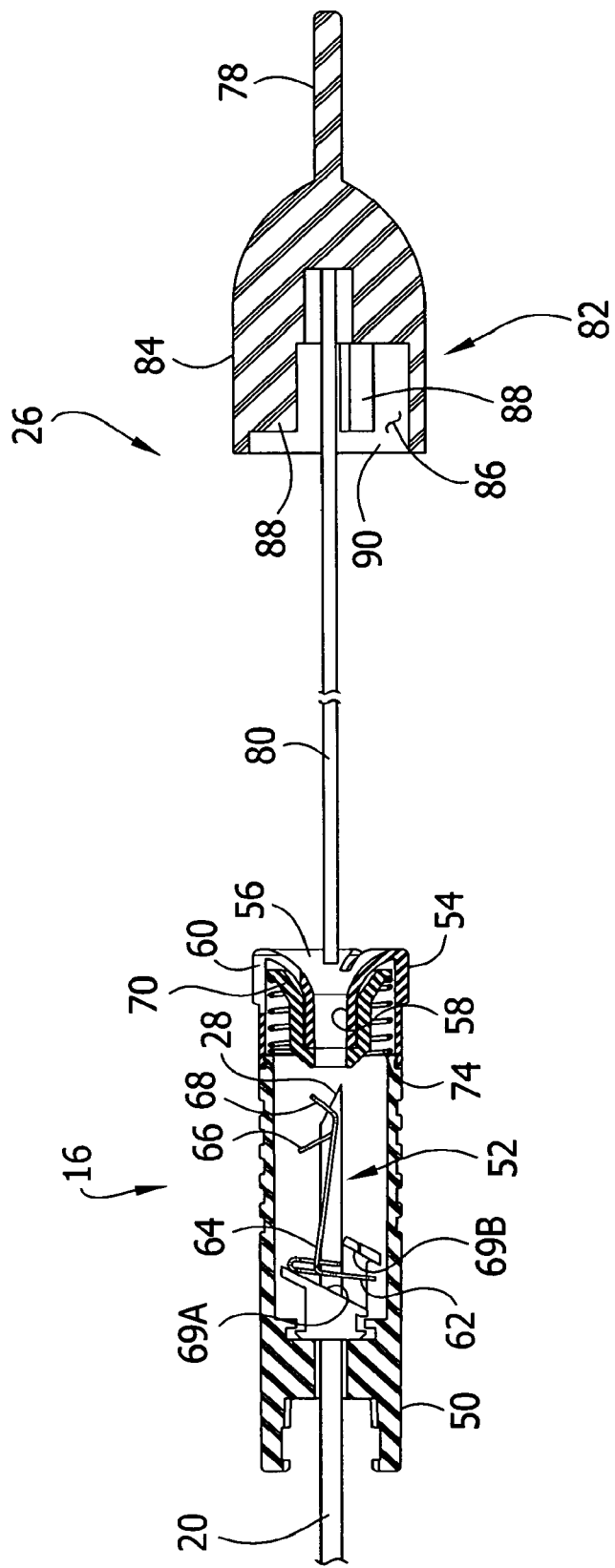
FIG. 2 is a fragmentary partial section of the needle assembly with the obturator entering a safety shield of the needle assembly.
Figure 3:
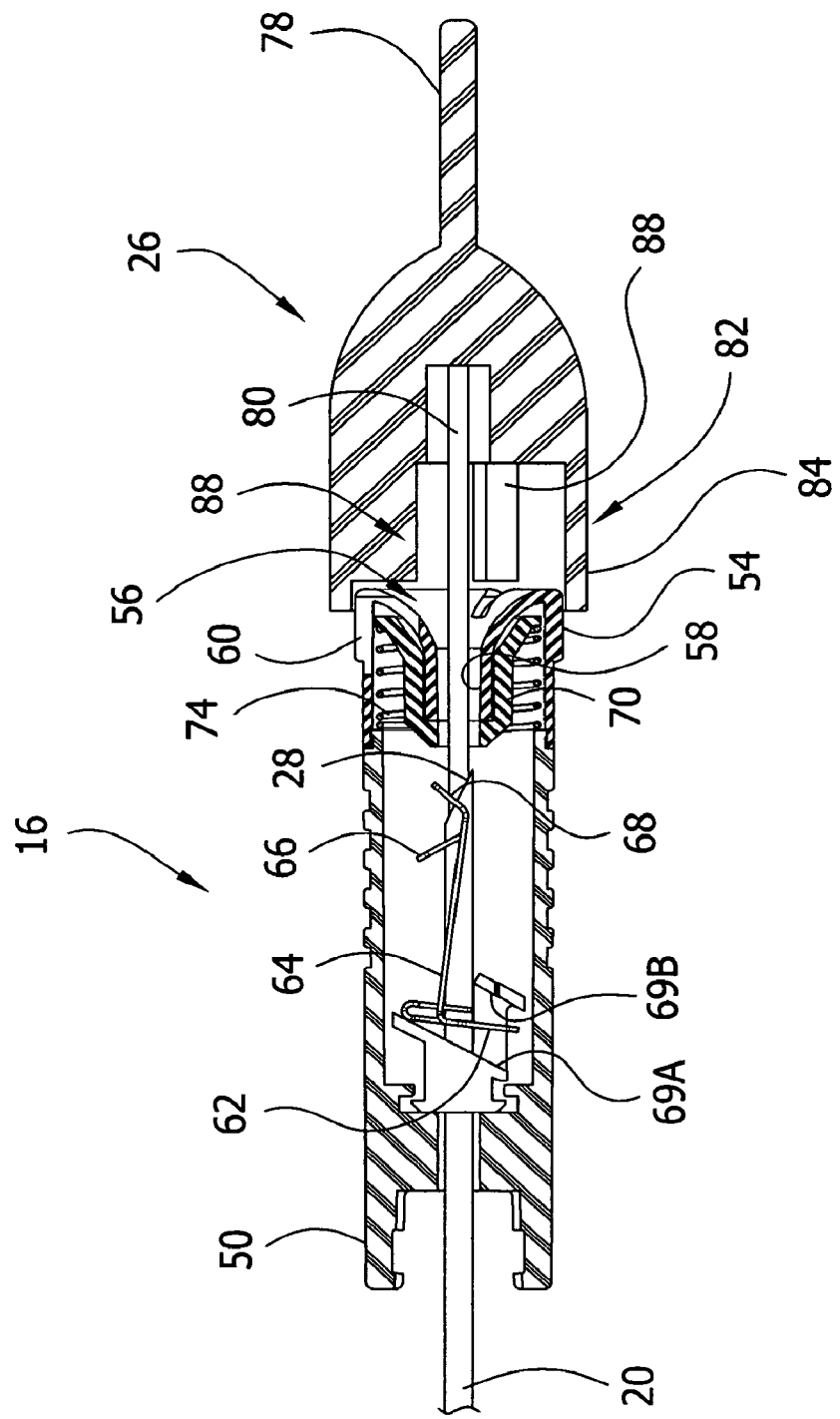
FIG. 3 is the fragmentary elevation of FIG. 2 but showing the obturator inserted to a position in which a sample collected by the needle assembly is pushed out of the needle assembly.

FIG. 2 illustrates the initial position of the obturator 26 with the shaft 80 entering the distal end of the tubular housing 50. The free end of the shaft 80 has not yet entered the central axial passageway of the cannula 20 or the aperture 58 of the distal end piece 54. The funnel-shaped surface 56 of the distal end piece 54 guides the shaft 80 toward the aperture 58 that is aligned with the central axial passageway of the cannula 20, thereby facilitating reception of the shaft in the passageway. The grip 78 is pushed to advance the shaft 80 through the aperture 58 in the funnel-shaped surface 56 and into the central axial passageway, which pushes the sample toward the proximal end of the central axial passageway. The shaft 80 is advanced until it protrudes out of the proximal end of the central axial passageway, thereby pushing the sample (not shown) out of the cannula 20 where it can be collected in a Petri dish or other suitable container. The relative location of the tubular shroud 84 and safety shield 16 are in this position are illustrated in FIG. 3. As the shaft 80 is advanced, it slides through the aperture 58 in the distal end piece 54. The locking mechanism 52 remains engaged so that the safety shield 16 does not move and the sharp tip 28 remains covered.

The technician may observe the sample ejected from the central axial passageway of the cannula 20. If it is determined that the sample is satisfactory, the obturator 26 can be pulled so that the shaft 80 slides back through and out of the cannula 20. The needle assembly 10 can be discarded, or possibly but less likely, cleaned and sterilized for a subsequent use. If the sample is not satisfactory, however, it will be necessary to obtain a second sample from the same patient. This can be done using the same needle assembly 10, but the tubular housing 50 is locked in place by the locking mechanism 52 over the sharp tip 28 of the cannula 20. The tubular housing 50 needs to be moved away from the tip 28 before the needle assembly 10 can be used to obtain a second sample.

The obturator 26 of the present invention is particularly adapted to permit the safety shield 16 to be released and moved back from the sharp tip 28 of the cannula 20. It should be understood, however, that a device other than an obturator 26 incorporating the resetting, or unlocking, features of the obturator described herein, but not functioning as an obturator, is also contemplated as within the scope of the present invention. From the position shown in FIG. 3, the grip 78 can be advanced toward the tubular housing 50 so that the ribs 88 are received into the corresponding peripheral slots 60 in the tubular housing 50. It will be necessary to align the ribs 88 with corresponding ones of the slots 60 before the ribs may enter the slots. The slots 60 and ribs 88 may be shaped and/or arranged to make this easier or harder to accomplish as desired. In the illustrated embodiment, the three slots 60 and three ribs 88 are all the same size and shape and located at 120 degree intervals. This arrangement makes it relatively easy to align the obturator 26 and safety shield 16 so that the ribs 88 will be received in the slots 60. However, as stated previously, other arrangements and configurations are envisioned. For example and without limiting the breadth of the present disclosure, the slots 60 and ribs 88 can be arranged at unequal intervals. Moreover, the slots 60 and ribs 88 may have different sizes so that the ribs will be received in the slots in only one relative orientation of the obturator 26 and the safety shield 16. Those of ordinary skill in the art will appreciate other possible configurations and/or arrangements. The bias of the spring 74 resists further advancement of the ribs 88 and hence of the obturator 26. This provides a tactile signal to the technician that the obturator shaft 80 has been inserted far enough into the central axial passageway of the cannula 20 to remove the sample, and that further insertion will result in release of the locking mechanism 52.

Figure 4:
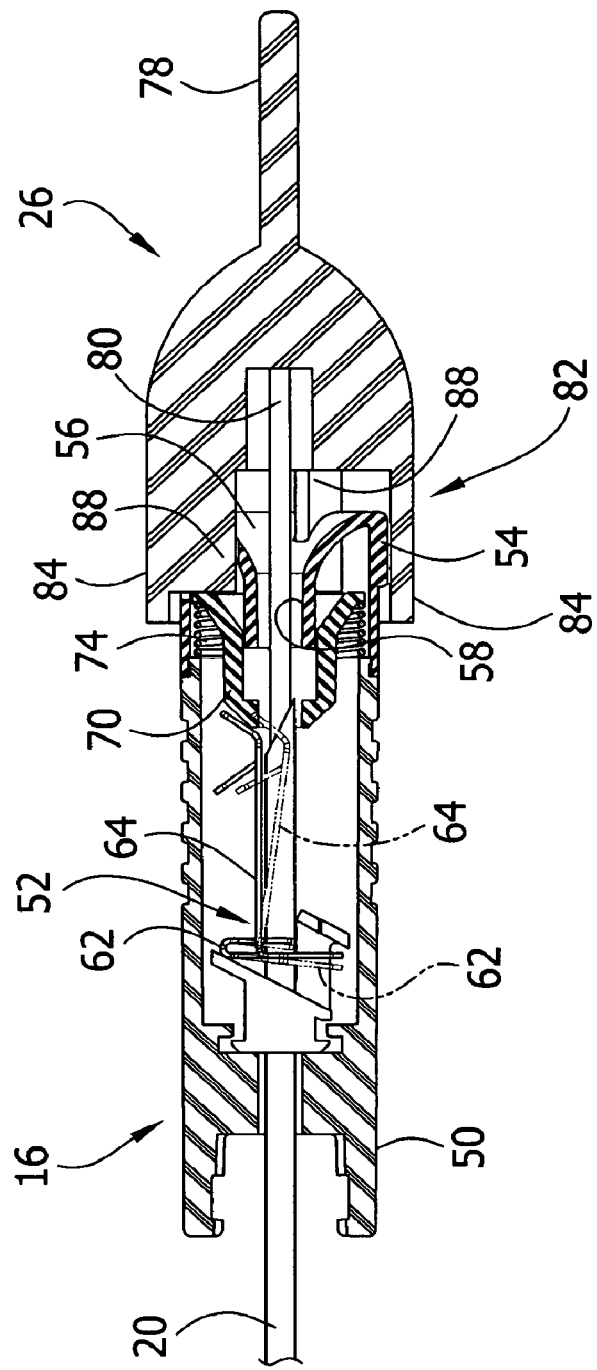
FIG. 4 is the fragmentary elevation of FIG. 2 but showing use of the obturator to reset a locking mechanism of the safety shield.
Figure 5:
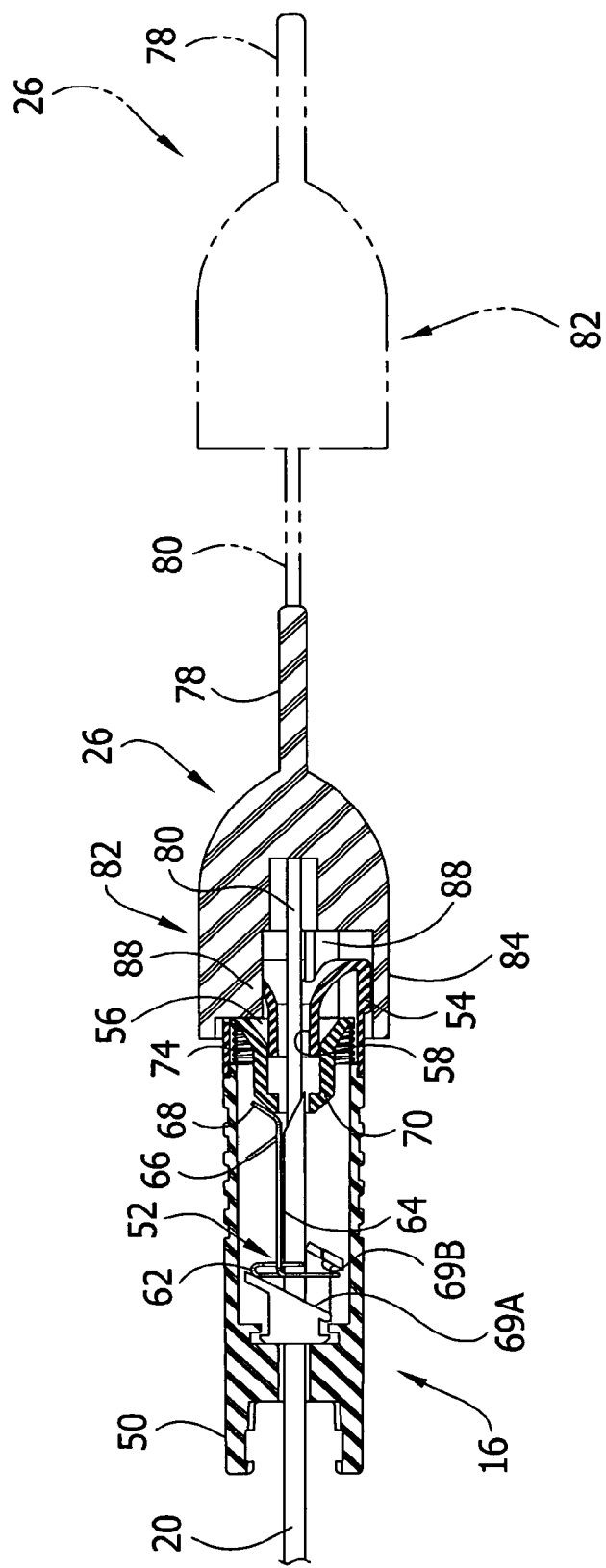
FIG. 5 is the fragmentary elevation of FIG. 2 but showing the safety shield set for withdrawal from a sharp end of the needle assembly after release of the locking mechanism.

If the safety shield 16 is to be reset to expose the sharp tip 28 of the cannula 28, the grip 78 can be advanced toward the tubular housing 50 so that the ribs 88 move into the slots 60 and push the reset plunger 70 against the bias of the spring 74 axially toward the proximal end of the tubular housing 50. The front surface 72 of the reset plunger 70 engages the tabs 68 of the canting member moving the arms 64 back to a position more nearly parallel to the longitudinal axis of the cannula 20. This moves the base 62 of the canting member to a position substantially orthogonal to the longitudinal axis of the cannula 20 so that the cannula can once again slide freely through the hole in the base (FIG. 4). The locking mechanism 52 is thereby released. Thus as shown in FIG. 5, the tubular housing 50 can be grasped to pull back the safety shield 16 toward the distal housing member 24 so that the sharp tip 28 of the cannula 20 is once again exposed. The obturator shaft 80 can be removed and the stylet 18 can be reinserted into the cannula 20 for a second collection of a sample. When the ribs 88 move back out of the slots 60, the spring 74 moves the reset plunger 70 back toward the distal end of the tubular housing 50 so that the locking mechanism 52 is again free to operate for locking the safety shield 16 over the sharp tip 28 of the cannula 20.

Figure 9:
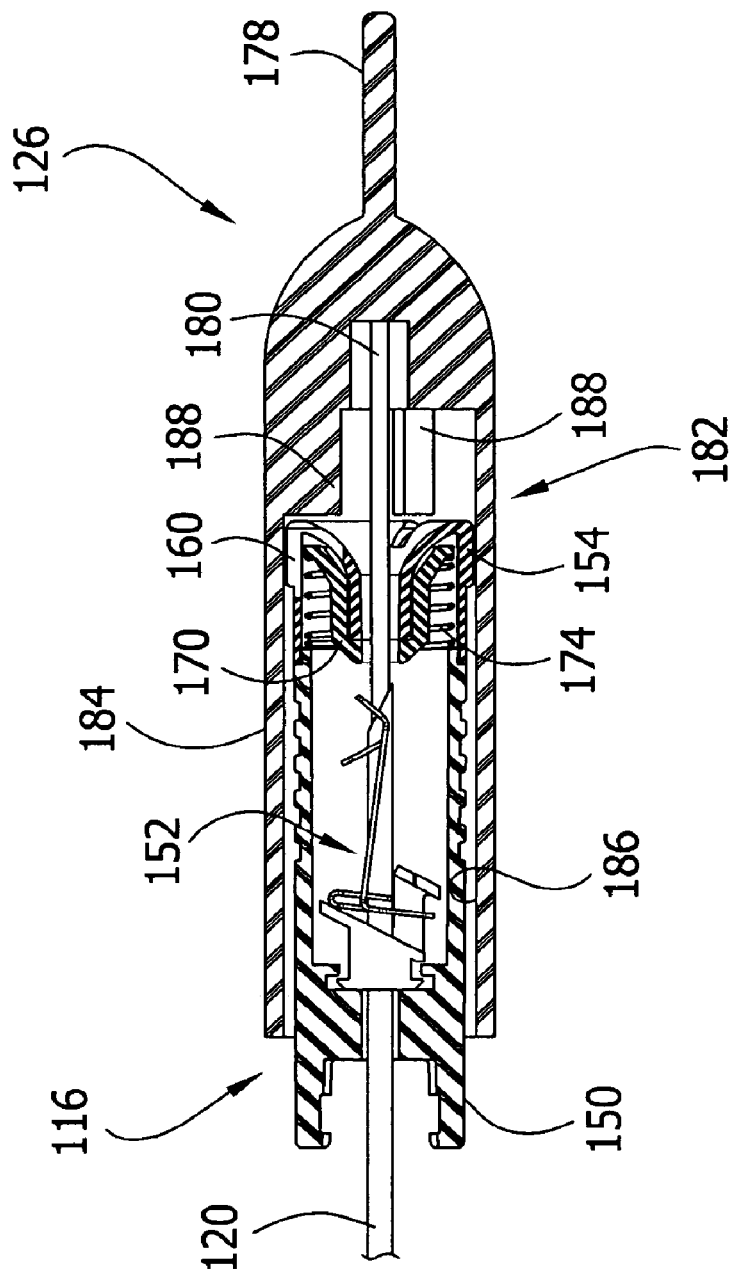
FIG. 9 is a fragmentary partial section of a needle assembly of a second embodiment in a configuration similar to FIG. 3.
Figure 10:
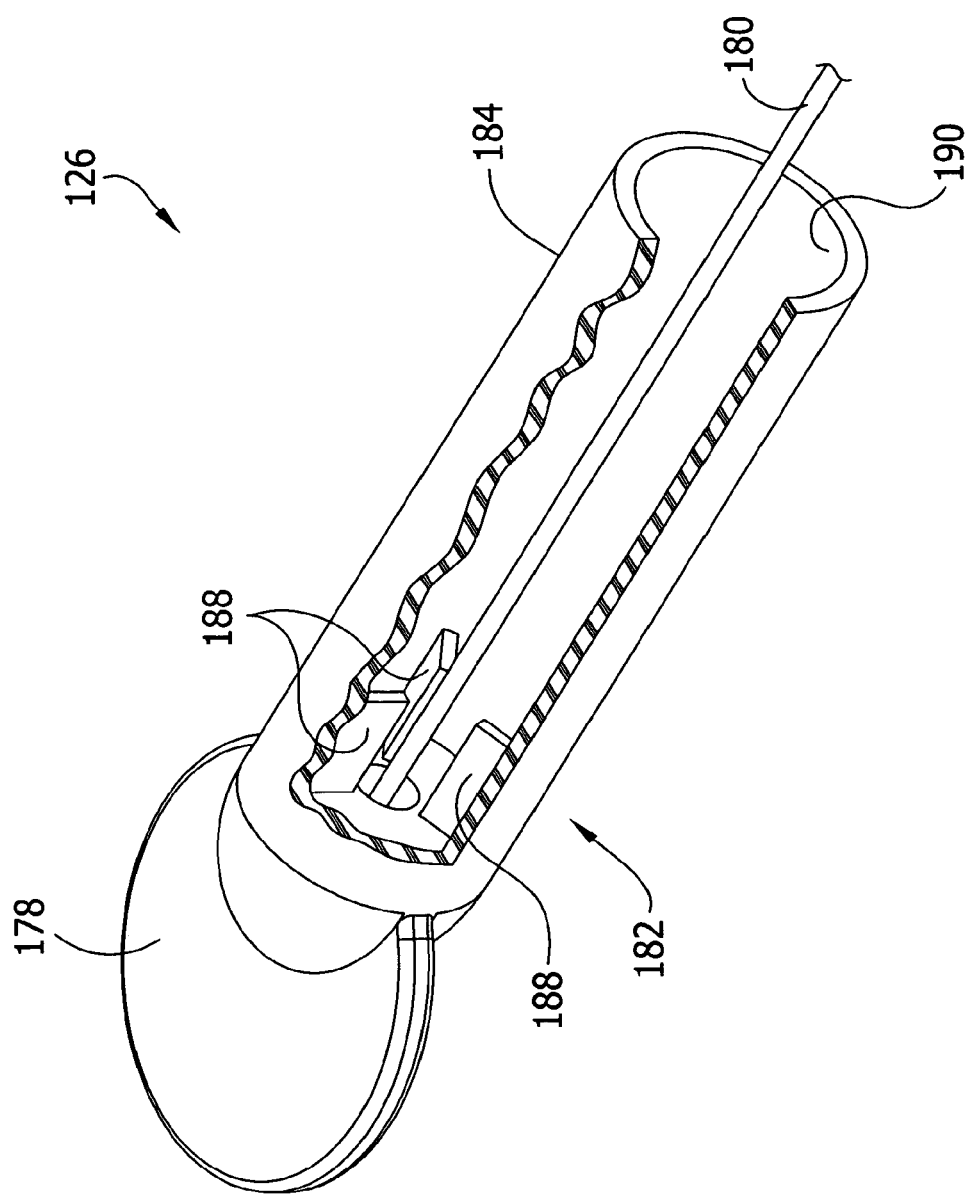
FIG. 10 is a fragmentary perspective of an obturator of the needle assembly of FIG. 9.
Figure 11:
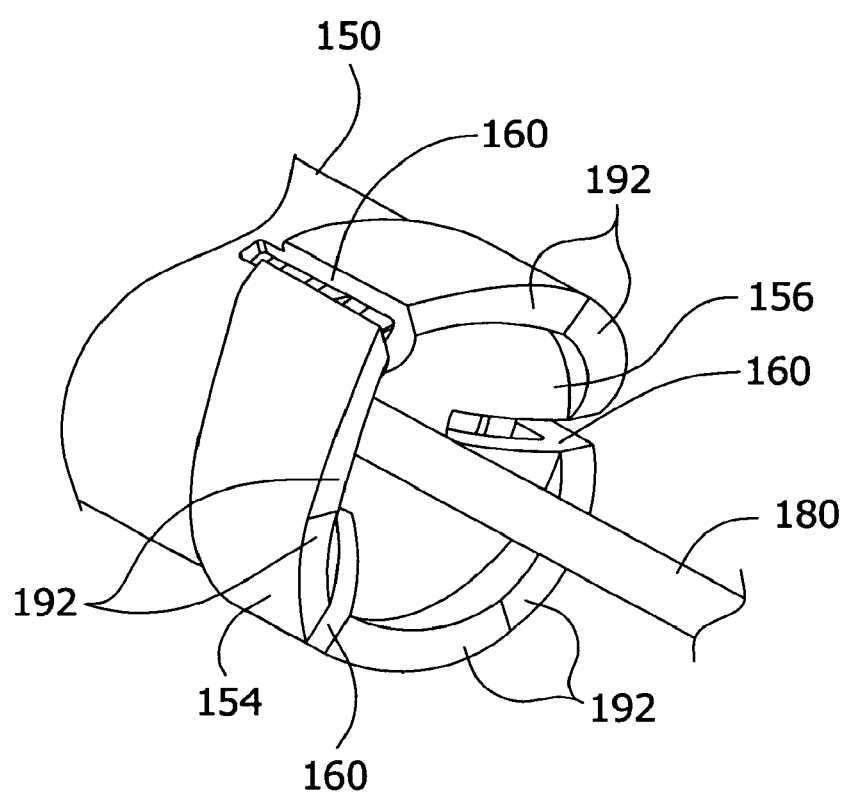
FIG. 11 is a fragmentary perspective of an end of a shield of the needle assembly of FIG. 9.

Referring now to FIGS. 9 and 10, a needle assembly of a second embodiment is shown. Parts of the needle assembly of the second embodiment are given the same reference numerals as the corresponding parts of the needle assembly of the first embodiment, plus "100". A safety shield 116 may have substantially the same construction as the safety shield 16. In particular, the shield 116 includes a tubular housing 150 having peripheral slots 160, as in the first embodiment. An obturator 126 and reset key 182 also have similar constructions (e.g., including ribs 188) as in the first embodiment. However, a tubular shroud 184 of the second embodiment has a length which is sufficiently great so that a central open space 186 of the shroud can receive substantially the entire tubular housing 150. Preferably at least a majority of the tubular housing 150 is received in the open space 186 of the shroud 184. The operation of ribs 188 associated with the tubular shroud 184 to release a locking mechanism 152 may be as described for the first embodiment. However by receiving tubular housing 150 in the central open space 186 of the shroud 184, the tubular housing is shielded from being inadvertently grasped as the obturator is pulled away from the safety shield so that the safety shield 116 is not unintentionally pulled off of the cannula 20. As best seen in FIG. 11, the peripheral edge of a distal end piece 154 of the tubular housing 150 is shaped to include edge segments 192 arranged at converging angles to funnel the ribs 188 into the slots 160 when the ribs engage the distal end piece. Because the ribs 188 are located deep inside the tubular shroud 184 at the bottom of the open space 186, alignment of the ribs with the slots 160 could be difficult. However, the shaped peripheral edge segments 192 engage the ribs 188 and urge the rotation of the obturator 126 to properly orient the reset key 182 so that the ribs move into the slots 160.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements. Moreover, the use of "up", "down", "top", and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A needle assembly comprising:
   mounting structure;
   a needle extending from the mounting structure along a longitudinal axis, the needle having a sharp end and a central axial passageway extending along the longitudinal axis;
   a safety shield moveable with respect to the needle for selectively covering the sharp end of the needle, the shield including a tubular housing having a funnel-shaped end surface opposite the mounting structure when the shield covers the sharp end of the needle, said surface leading to a central aperture that is aligned with the central axial passageway of the needle when the shield covers the sharp end of the needle; and
   a reset key configured to engage the safety shield, the reset key comprising a shaft sized for inserting into the central aperture of the housing, the funnel-shaped end surface guiding the shaft into the aperture of the housing to register the reset key with the safety shield and the shaft with the central axial passageway of the needle to obturate the passageway;
   wherein the tubular housing of the safety shield has an outer surface surrounding the funnel-shaped end surface; and
   the reset key includes a shroud having an inner wall sized and shaped for receiving the outer surface of the tubular housing to center the safety shield in the reset key.

2. A needle assembly as set forth in claim 1 wherein:
   the reset key includes a rib positioned inside a central opening defined by the inner wall of the shroud; and
   the end surface of the safety shield has a slot sized, shaped, and positioned for receiving the rib to release an internal locking mechanism in the shield permitting the shield to move to uncover the sharp end of the needle.

3. A needle assembly as set forth in claim 2 wherein:
   said rib is a first rib and the reset key includes a plurality of ribs including said first rib, each of said plurality of ribs being positioned inside the central opening defined by the inner wall of the shroud; and
   said slot is a first slot and the end surface of the safety shield has a plurality of slots including said first slot, the plurality of slots being at least as numerous as the plurality of ribs of the reset key, each of said plurality of slots being sized, shaped, and positioned for receiving a corresponding rib of said plurality of ribs.

4. A needle assembly as set forth in claim 1 wherein:
   the reset key includes a rib; and
   the end surface of the safety shield has a slot sized, shaped and positioned for receiving the rib to release an internal locking mechanism in the shield permitting the shield to move to uncover the sharp end of the needle.

5. A needle assembly as set forth in claim 4 wherein:
   said rib is a first rib and the reset key includes a plurality of ribs including said first rib; and
   said slot is a first slot and the end surface of the safety shield has a plurality of slots including said first slot, the plurality of slots being at least as numerous as the plurality of ribs of the reset key, each of said plurality of slots being sized, shaped, and positioned for receiving a corresponding rib of said plurality of ribs.

6. A needle assembly comprising:
   mounting structure;
   a needle extending from the mounting structure to a sharp end;
   a safety shield moveable with respect to the needle for selectively covering the sharp end of the needle, the shield including a tubular housing having an outer surface; and
   a reset key including a shroud having an inner wall sized and shaped for receiving the outer surface of the tubular housing to register the reset key with the safety shield, the reset key being configured to releasably engage the safety shield.

7. A needle assembly as set forth in claim 6 wherein the outer surface of the safety shield housing and the inner wall of the reset key shroud have complementary circular cross sections.

8. A needle assembly as set forth in claim 6 wherein:
   the reset key includes a rib positioned inside a central opening defined by the inner wall of the shroud; and the end surface of the safety shield has a slot sized, shaped, and positioned for receiving the rib to release an internal locking mechanism in the shield permitting the shield to move to uncover the sharp end of the needle.

9. A needle assembly as set forth in claim 8 wherein:

said rib is a first rib and the reset key includes a plurality of ribs including said first rib, each of said plurality of ribs being positioned inside the central opening defined by the inner wall of the shroud; and said slot is a first slot and the end surface of the safety shield has a plurality of slots including said first slot, the plurality of slots being at least as numerous as the plurality of ribs of the reset key, each of said plurality of slots being sized, shaped, and positioned for receiving a corresponding rib of said plurality of ribs.

10. A needle assembly comprising:

mounting structure;

a needle extending from the mounting structure to a sharp end;

a safety shield moveable with respect to the needle for selectively covering the sharp end of the needle, the shield including a tubular housing having an end surface opposite the mounting structure when the shield covers the sharp end of the needle, the end surface having a slot therein; and a reset key configured to engage the safety shield, the reset key including a rib sized, shaped, and positioned for receipt in the slot in the end surface of the safety shield when the reset key engages the shield to release an internal locking mechanism in the shield permitting the shield to move to uncover the sharp end of the needle.

11. A needle assembly as set forth in claim 10 wherein the internal locking mechanism is biased to prevent the shield to move to uncover the sharp end of the needle.

12. A needle assembly as set forth in claim 10 wherein:

said rib is a first rib and the reset key includes a plurality of ribs including said first rib, each of said plurality of ribs being positioned on the end surface; and said slot is a first slot and the end surface of the safety shield has a plurality of slots including said first slot, the plurality of slots being at least as numerous as the plurality of ribs of the reset key, each of said plurality of slots being sized, shaped, and positioned for receiving a corresponding rib of said plurality of ribs.

13. A needle assembly as set forth in claim 12 wherein:

the plurality of ribs consists of three ribs; and the plurality of slots consists of three slots.

14. A needle assembly as set forth in claim 13 wherein the ribs and slots are equally spaced.

15. A needle assembly as set forth in claim 12 wherein each of the plurality of ribs comprises a radially extending blade.

16. A needle assembly as set forth in claim 12 wherein:

the needle has a central axial passageway;

the end surface of the safety shield includes a central aperture that is aligned with the central axial passageway of the needle when the shield covers the sharp end of the needle; and the reset key includes a shaft sized for inserting into the central aperture of the end surface of the housing to register the reset key with the safety shield and the shaft with the central axial passageway of the needle to obturate the passageway.

17. A needle assembly as set forth in claim 10 wherein:

the needle has a central axial passageway;

the end surface of the safety shield includes a central aperture that is aligned with the central axial passageway of the needle when the shield covers the sharp end of the needle; and the reset key includes a shaft sized for inserting into the central aperture of the end surface of the housing to register the reset key with the safety shield and the shaft with the central axial passageway of the needle to obturate the passageway.

* * * * *